United States Patent [19]
Wilson

[11] Patent Number: 5,928,288
[45] Date of Patent: Jul. 27, 1999

[54] VARIABLE FIT OBLONG ACETABULAR PROSTHESIS

[75] Inventor: Stephen F. Wilson, Raynham, Mass.

[73] Assignee: Johnson & Johnson Professional, Inc., Raynham, Mass.

[21] Appl. No.: 09/076,963

[22] Filed: May 13, 1998

[51] Int. Cl.[6] ........................................... A61F 2/34
[52] U.S. Cl. ............................................... 623/22; 623/18
[58] Field of Search ................................. 623/18, 22, 23, 623/20–21

[56] References Cited

U.S. PATENT DOCUMENTS

| | | | |
|---|---|---|---|
| D. 296,714 | 7/1988 | Averill et al. | D24/33 |
| 4,634,444 | 1/1987 | Noiles | 623/20 |
| 4,662,891 | 5/1987 | Noiles | 623/22 |
| 4,695,282 | 9/1987 | Forte et al. | 623/22 |
| 4,704,127 | 11/1987 | Averill et al. | 623/22 |
| 4,798,610 | 1/1989 | Averill et al. | 623/22 |
| 4,846,839 | 7/1989 | Noiles | 623/18 |
| 4,865,603 | 9/1989 | Noiles | 623/18 |
| 4,892,549 | 1/1990 | Figgie, III et al. | 623/22 |
| 5,176,710 | 1/1993 | Hahn et al. | 623/20 |
| 5,176,711 | 1/1993 | Grimes | 623/22 |
| 5,192,329 | 3/1993 | Christie et al. | 623/22 |
| 5,219,362 | 6/1993 | Tuke et al. | |
| 5,282,864 | 2/1994 | Noiles et al. | 623/18 |
| 5,290,315 | 3/1994 | DeCarlo, Jr. | 623/22 |
| 5,326,368 | 7/1994 | Collazo | 623/22 |
| 5,358,532 | 10/1994 | Evans et al. | 623/22 |
| 5,370,704 | 12/1994 | DiCarlo, Jr. | 623/22 |
| 5,413,603 | 5/1995 | Noiles et al. | 623/18 |
| 5,549,694 | 8/1996 | Noiles et al. | 623/22 |
| 5,549,697 | 8/1996 | Caldarise | 623/22 |
| 5,549,701 | 8/1996 | Mikhail | 623/22 |
| 5,571,201 | 11/1996 | Averill et al. | 623/22 |
| 5,676,704 | 10/1997 | Ries et al. | 623/18 |

FOREIGN PATENT DOCUMENTS 4211347  10/1993  Germany.

OTHER PUBLICATIONS

Johnson & Johnson Orthopaedics Brochure entitled The P.F.C.™ Total Hip System Surgical Technique, pp. 1–52.

*Primary Examiner*—Bruce Snow
*Attorney, Agent, or Firm*—Nutter, McClennen & Fish, LLP

[57] ABSTRACT

An acetabular prosthesis has an oblong geometry in which its dimensions in a first axis exceed those in a second axis that is normal to the first axis. The prosthesis has a superior, bone engaging surface with primary and secondary partial spheres that are merged together. The opposed inferior surface of the prosthesis includes at least one hemispherical cavity that is formed within the primary partial sphere. The primary partial sphere has dimensions that exceed the secondary partial sphere by less than or equal to about 5%.

11 Claims, 3 Drawing Sheets

VARIABLE FIT OBLONG ACETABULAR PROSTHESIS

CROSS-REFERENCE TO RELATED APPLICATIONS

Not Applicable.

STATEMENT REGARDING FEDERALLY-SPONSORED RESEARCH

Not Applicable.

FIELD OF THE INVENTION

The present invention relates to bioimplantable joint prostheses and, more particularly, to prostheses used in artificial hip joints.

BACKGROUND OF THE INVENTION

Joint arthroplasty is a well known surgical procedure by which a diseased and/or damaged natural joint is replaced by a prosthetic joint. Joint arthroplasty is commonly performed for hips, knees, elbows, and other joints. The health and condition of the joint to be replaced dictate the type of prosthesis necessary to replace the natural joint.

In a total hip arthroplasty an acetabular cup is implanted in the acetabular cavity of the pelvis to replace the natural acetabulum. Replacement of the acetabulum is necessary for various joint conditions, such as when there is an inadequate articulation surface for a head or ball of a prosthetic femoral component. Total hip arthroplasty is also warranted in certain cases of Developmental Dysplasia Hip (DDH) where the natural acetabular cavity does not properly form to allow sufficient joint articulation.

To implant an acetabular cup, a cavity is reamed in the acetabulum. The acetabular cup prosthesis is then inserted into the formed cavity and secured by mechanical means, interference fit, or by a combination thereof. The acetabular cup prosthesis is positioned in the pelvis at a fixed orientation with respect to patient anatomy and should remain stable.

In cases where the acetabular cavity is not generally spherical, an oblong acetabular cup may need to be implanted. Such situations include certain DDH cases and joint conditions where a previously implanted acetabular cup prosthesis (typically a hemispherical cup) has migrated in a superior direction. The oblong geometry of the cup compensates for the elongated acetabular cavity. One type of elongated acetabular cup has an outer contour defined by two similarly dimensioned adjacent hemispheres. An exemplary dual hemisphere acetabular cup 10 is shown in FIGS. 1A and 1B. The cup 1 has an outer surface 2 defined by a first primary hemisphere 4 merged with a secondary hemisphere 6. The primary hemisphere defines a primary face 8 and the secondary hemisphere defines a secondary face 9. The primary hemisphere 4 has a concave inner surface 7 that is matable with a liner which, in turn, receives a head or ball portion of a femoral hip component.

Most acetabular cup prostheses rely, at least to some extent, on an interference fit between the bone engaging surface of the implant and the cavity formed within bone. Thus, the acetabular cup, including the two hemispheres of oblong acetabular cups, tend to be oversized (by about three percent) with respect to the diameter of the cavity into which they are implanted.

As noted above, oblong or dual-hemisphere acetabular cups tend to have similarly sized lobes or hemispheres. This design can render challenging the seating of the acetabular cup prosthesis within a patient. For example, the primary hemisphere must be properly aligned and seated while the secondary hemisphere must be seated so that it does not protrude from its machined cavity. In some instances attempts to seat properly the secondary hemisphere may affect the seating and alignment of the primary hemisphere.

Most oblong or dual cups also place equal amounts of load on both of the primary and secondary hemispheres and hence the cavities into which they are placed. The secondary hemisphere may offer a lower quality of bone, or less bone, and would benefit from receiving a lesser share of the load.

Various designs of dual lobe or oblong acetabular cups are known in the art. For example, U.S. Pat. Nos. 5,192,329; 5,290,315; and 5,370,704, all of which share a common specification, describe an oblong acetabular cup in which the primary and secondary hemispheres are separate, but are joined together pre-operatively. U.S. Pat. No. 5,326,368 discloses a modular acetabular cup that includes extension member, or augments, that are attachable to the cup to enable it to achieve a cross-section of a desired configuration. U.S. Pat. No. 5,176,711 describes an acetabular cup prosthesis having an augmentation piece or defect lobe that is separately attachable to the primary acetabular cup by a Morse-taper arrangement. U.S. Pat. No. 4,892,549 describes a single acetabular cup having first and second spherical surface portions where the radius of the first spherical surface portion is slightly greater than the radius of the second spherical surface portion.

Despite the designs that now exist for oblong acetabular cups, it would be desirable to provide an oblong acetabular cup which may be seated more easily within a patient's body and which distributes more load to the anatomical cavity than to the defect cavity.

SUMMARY OF THE INVENTION

The present invention provides an acetabular prosthesis suitable for placement within a cavity having a compound geometric shape. In one embodiment the acetabular prosthesis comprises a body having a main axis and a superior, bone-engaging surface. The superior surface of the body includes a primary partial sphere having a center and a first diameter, and a secondary partial sphere having a center that is displaced from the center of the primary partial sphere and a second diameter is less than the first diameter. The inferior surface of the body is disposed opposite of the superior surface and has at least one substantially hemispherical mating cavity extending therein. In one embodiment the mating cavity is adapted to receive a bearing component of a hip joint prosthesis. A ball or head component of a femoral hip component mates within and articulates with the bearing component. The dimensions of the mating cavity will vary depending upon the dimensions of the acetabular prosthesis and/or the dimensions of the bearing component.

The smaller relative size of the secondary partial sphere with respect to the primary partial sphere is advantageous in that it allows the primary sphere to be subjected to greater loads than those placed upon the secondary partial sphere. Moreover, this construction facilitates easier placement and alignment of the acetabular cup within the patient's body. In one embodiment, the diameter of the primary partial sphere exceeds the diameter of the secondary partial sphere by an amount less than or equal to five percent.

BRIEF DESCRIPTION OF THE DRAWINGS

The invention will be more fully understood from the following detailed description in conjunction with the accompanying drawings in which.

DETAILED DESCRIPTION OF THE INVENTION

Figure 1A:
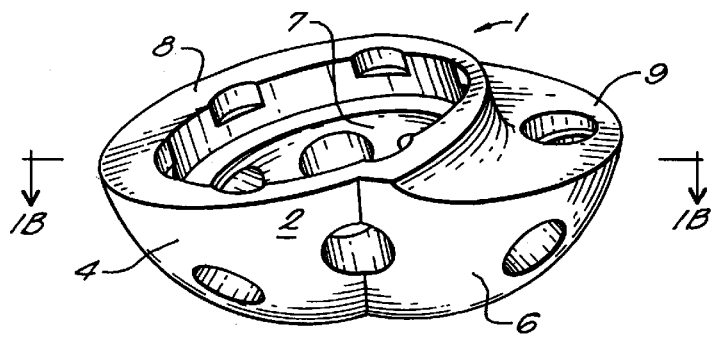
FIG. 1A is a perspective view of a prior art oblong acetabular cup.
Figure 1B:
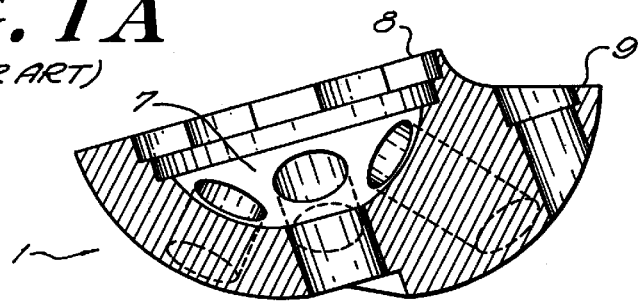
FIG. 1B is a cross-sectional view of the prior art acetabular cup of FIG. 1A along the lines 1B—1B.

As shown in FIGS. 2–6, in which like reference numerals designate like or corresponding parts throughout the different views, there is shown a bioimplantable joint prosthesis component in the form of an acetabular prosthesis 10. The acetabular prosthesis 10 is adapted to be placed within a cavity that is formed within a patient's acetabulum. The cavity (not shown) typically has a compound geometric shape complementary to that of a bone-engaging surface of the prosthesis. As illustrated, the acetabular prosthesis is of an oblong shape, in which the dimension along a first axis 12 is greater than the dimension along a second axis 14.

In the illustrated embodiment, the prosthesis 10 is made from a unitary block of material, e.g., a metal or metal alloy, and it includes a primary lobe 16 and a secondary lobe 18. Each of the primary and secondary lobes 16 and 18 is in the form of at least a partial sphere. That is, in the direction of the second axis 14, the primary and secondary lobes 16, 18 are substantially hemispherical. In the direction of the first axis 12, the primary and secondary lobes 16, 18 represent partial hemispheres that are merged with one another to form the oblong prosthesis.

Figure 2:
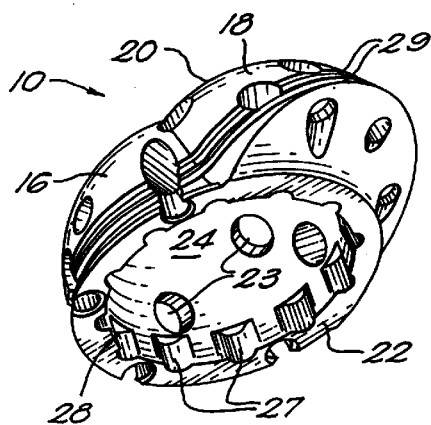
FIG. 2 is a perspective view of an oblong acetabular cup constructed according to the present invention.
Figure 3:
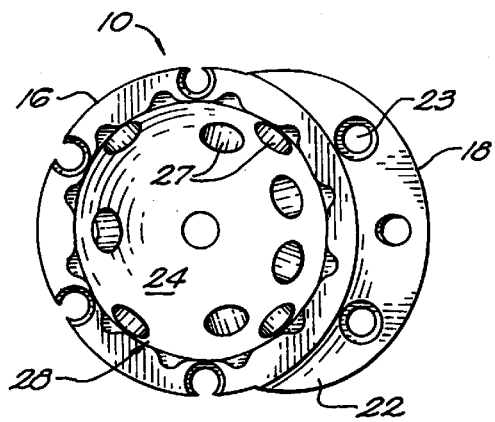
FIG. 3 is a bottom plan view of the acetabular cup of FIG. 2.
Figure 4:
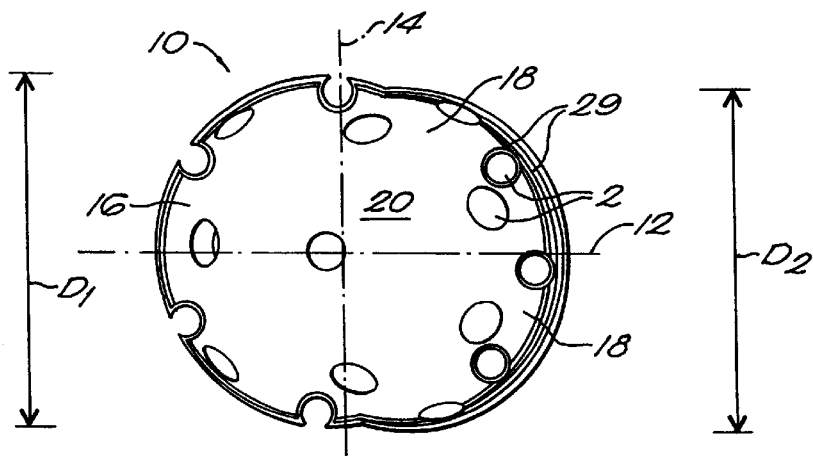
FIG. 4 is a top plan view of the acetabular cup of FIG. 2.
Figure 6:
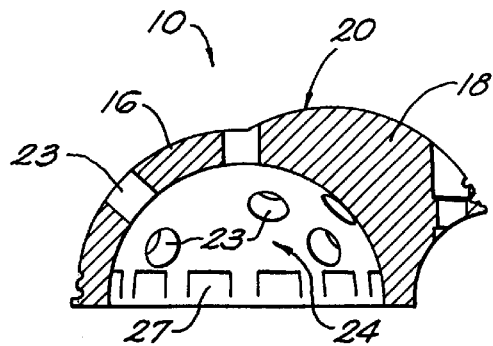
FIG. 6 is a sectional view along the lines 6—6 of FIG. 2.

The prosthesis 10 further includes a superior, bone-engaging surface 20 and an opposed, inferior surface 22. One or more apertures 23 may extend through the prosthesis, from inferior surface 22 to superior surface 20, so as to receive bone screws (not shown) for affixing the prosthesis within the patient's acetabulum. As shown in FIGS. 2 and 6, the inferior surface 22 includes at least one substantially hemispherical cavity 24 that is formed within the primary lobe 16. Those having ordinary skill in the art will readily appreciate that the mating cavity 24 is adapted to receive a bearing component 25 which is affixed within the mating cavity by a variety of known mechanisms, such as by interaction with mounting grooves 27 shown in phantom. Further, a ball or head of a femoral hip component (not shown) mates with and articulates within the bearing component.

One of ordinary skill in the art will further appreciate that the superior, bone-engaging surface 20 may include one or more textured surface features, such as steps 29, which enhance fixation of the prosthesis to bone. The surface features may take the form of, or may be used in combination with, other such known structures, such as beads, pores, and the like (not shown).

Figure 5:
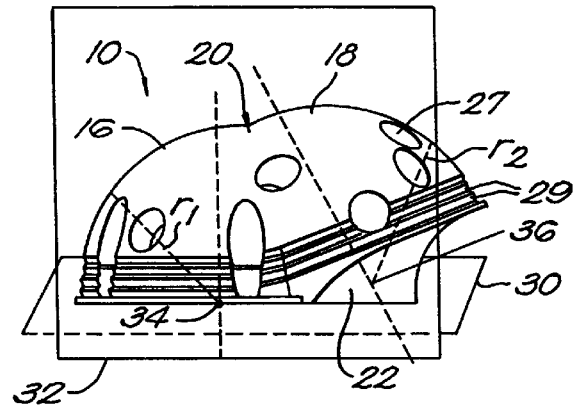
FIG. 5 is a side view of the acetabular cup of FIG. 2.

As shown in FIG. 5, the opening 28 of hemispherical mating cavity 24 defines the first plane 30 of the prosthesis, which is used to determine the proper anatomic position of the prosthesis. The second plane 32 of the prosthesis is normal to the first plane 30 and passes through both the center 34 of the primary lobe 16 and the center 36 of the secondary lobe 18. The centers 34, 36 of the primary and secondary lobes 16, 18 are spaced apart from each other in the direction of main axis 12 by a predetermined distance in the range of about 3 mm to 75 mm.

An advantage of the present invention is that the primary lobe 16 has dimensions that are greater than those of the secondary lobe 18. While the primary lobe 16 has dimensions that are designed to be approximately 3% greater than the diameter of a primary cavity in the reamed acetabulum, the secondary lobe is of a smaller size so that it is oversized by only about 0 to 2.5% with respect to a reamed defect cavity within the acetabulum. This geometry enables the primary lobe 16 to be properly seated within the acetabular cavity 38 without interference from the secondary lobe 18. At the same time, the secondary lobe 18 may be easily seated within the cavity without affecting the orientation of the primary lobe 16. As a result, the primary lobe 16 absorbs most of the load in vivo, which is a desirable result since the bone surrounding the primary lobe usually is of a better quality than that surrounding the secondary lobe.

As measured in the direction of the second axis 14, the diameter $D_1$ of the primary lobe is greater than the diameter $D_2$ of the secondary lobe by about 0.5% to 5%, and more preferably by about 0.5% to 3%. One of ordinary skill in the art will appreciate that the diameter of the primary lobe 16 is generally in the range of about 38 to 80 mm.

Similarly, in the direction of the first axis 12, the radius $r_1$ of the primary lobe 16 is greater than the radius $r_2$ of the secondary lobe by an amount in the range of about 0.5% to 5%, and most preferably by about 0.5% to 3%. The radius of the primary lobe 16 is generally in the range of about 19 to 40 mm.

Figure 7:
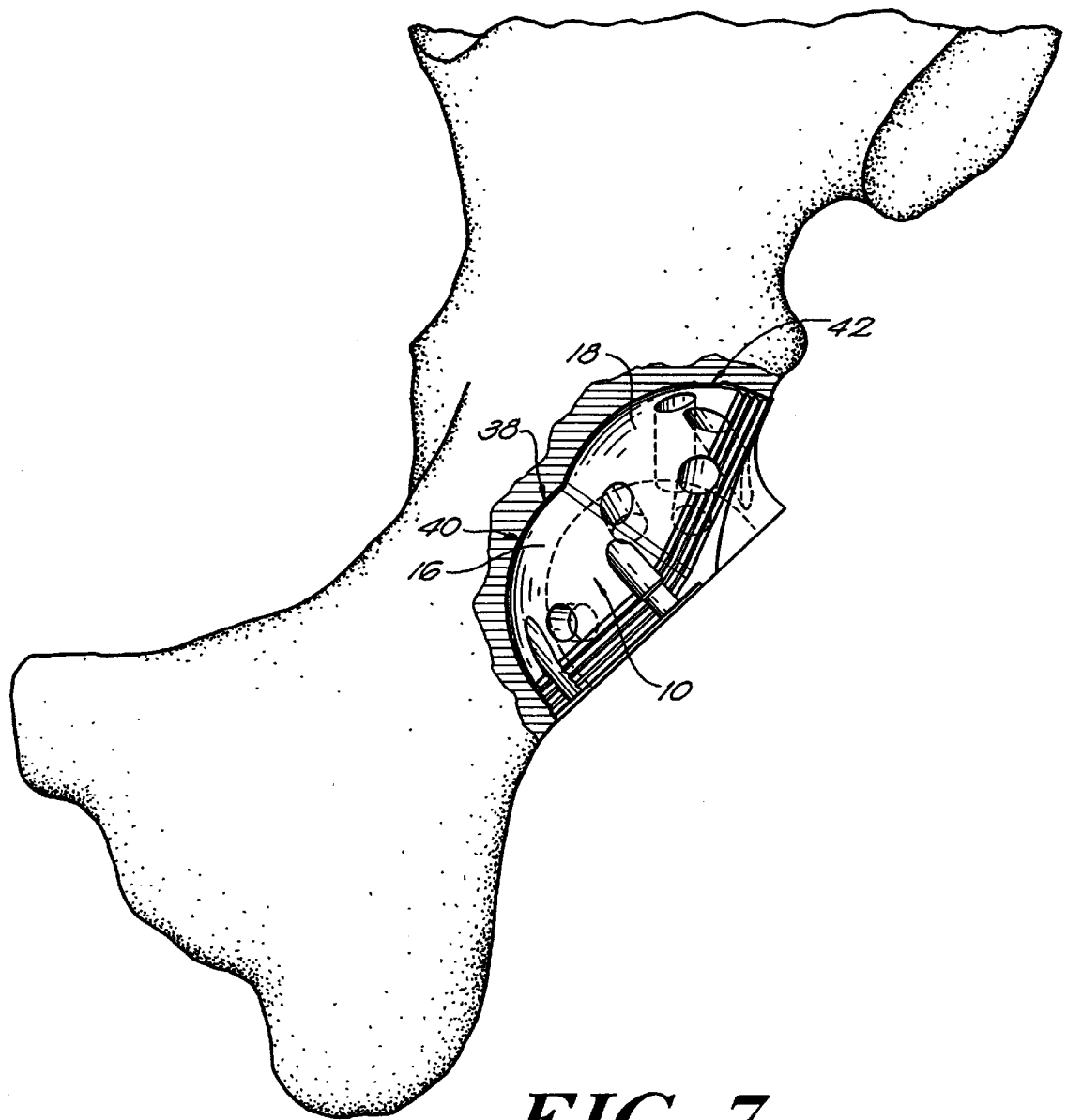
FIG. 7 is a view of the acetabular cup of FIG. 2, implanted within the bone of a patient.

FIG. 7 illustrates a prosthesis according to the present invention, mounted within a patient's acetabulum. As shown, the prosthesis 10 is mounted within a formed, dual-lobed cavity 38 which has a primary component 40 and a defect component 42. The primary lobe 16 of the prosthesis 10 is mounted within the primary component 40 of the cavity 38 while the defect lobe 18 of the prosthesis is mounted within the defect component 42 of the cavity 38. The primary lobe 16 of prosthesis 10 is designed to achieve approximately a 3% press fit with the primary component 40 of the cavity 38. Because the dimensions of the secondary lobe 18 are smaller than those of the primary lobe 16, the secondary lobe 18 achieves a lesser degree of press fit with the defect component 42 of cavity 38. That is, the degree of press fit of the secondary lobe 18 with the defect component 42 of cavity 38 is in the range of about 0 to 2.5%. As noted above, this geometry enables the proper seating of the primary lobe 16 without interference from the secondary lobe 18. Consequently, the primary lobe 16 achieves good rim contact with the opening of the reamed primary component 40 of the cavity 38 and it is positioned so that it can facilitate a proper range of motion and accept the femoral head (not shown) of a hip prosthesis.

One of ordinary skill in the art will realize the further features and advantages of the invention from the above-described embodiments. Accordingly, the invention is not to be limited by what has been particularly shown and described, except as indicated by the appended claims. All publications and references cited herein are expressly incorporated herein by reference in their entirety.

What is claimed is:

1. An acetabular prosthesis for implantation into a dual-lobed cavity, comprising;

a unitary, oblong body having a first axis and a second axis, the first axis having a length that is greater than a length of the second axis;

a superior, bone engaging surface of the body, the superior surface defined by a first lobe formed from a primary partial sphere having a center and a first radius, and a second lobe formed from a secondary partial sphere having a center that is displaced from the center of the primary partial sphere and a second radius that is less than the first radius such that the second lobe has less surface area than first lobe, the centers of the primary and secondary partial spheres being coplanar with the first axis such that the superior bone-engaging surface of the body has a boundary formed by an intersection of the first and second lobes defined by the primary and secondary partial spheres, the boundary being located between the center of the primary partial sphere and the center of the secondary partial sphere, wherein the first and second lobes are sized such that, after implantation, the primary partial sphere is subjected to greater loads than loads placed upon the secondary partial sphere; and an inferior surface, opposite the superior surface, having at least one substantially hemispherical mating cavity formed substantially within the primary partial sphere, the at least one mating cavity being dimensioned to receive a bearing component of a hip joint prosthesis.

2. The prosthesis of claim 1, wherein the first radius exceeds the second radius by about 0.5 to 3%.

3. The prosthesis of claim 1, wherein the center of the primary partial sphere is displaced from the center of the secondary partial sphere by a distance, measured along a first plane of the prosthesis, in the range of about 3 to 75 mm.

4. The prosthesis of claim 1, wherein the primary and secondary partial spheres are integrally formed with the body.

5. The prosthesis of claim 1, wherein the first diameter of the primary partial sphere is adapted to be approximately 3% oversized with respect to a cavity within which it is to be implanted, and the second radius of the secondary partial sphere is approximately 0% to 2.5% oversized with respect to a defect cavity within which it is to be implanted.

6. The prosthesis of claim 1, wherein at least a portion of the superior, bone engaging surface of the body includes one or more bone engaging structures.

7. The prosthesis of claim 6, wherein the one or more bone engaging structures are stepped structures.

8. The prosthesis of claim 6, wherein the one or more bone engaging structures are pores of a textured surface.

9. An acetabular prosthesis system, comprising:

an oblong, unitary body having a first axis and a second axis, the first axis having a length that is greater than a length of the second axis;

a superior, bone engaging surface of the body, the superior surface defined by a first lobe formed from a primary partial sphere having a center and a first radius measured from the center of the primary partial sphere to the bone engaging surface, and a second lobe formed from a secondary partial sphere having a center and a second radius measured from the center of the secondary partial sphere to the bone engaging surface, the second radius being smaller than the first radius such that the second lobe has less surface area than the first lobe, the centers of the primary and secondary partial spheres being coplanar with the first axis such that the superior bone-engaging surface of the body has a boundary formed by an intersection of the first and second lobes, the boundary being located between the center of the primary partial sphere and the center of the secondary partial sphere, wherein the first and second lobes are sized such that, after implantation, the primary partial sphere is subjected to greater loads than loads placed upon the secondary partial sphere;

an inferior surface, opposite the superior, bone engaging surface, having at least one substantially hemispherical mating cavity formed substantially within the primary partial sphere; and a substantially hemispherical bearing component adapted to be disposed within the mating cavity, the bearing component being effective to receive and articulate with a head of a hip joint prosthesis.

10. The prosthesis system of claim 9, wherein the first radius exceeds the second radius by about 0.5 to 3%.

11. The prosthesis system of claim 9, wherein the bearing component is removably secured within the mating cavity.

* * * * *